United States Patent [19]

Westplate

[11] Patent Number: 4,592,358
[45] Date of Patent: Jun. 3, 1986

[54] THERAPEUTIC DEVICE

[76] Inventor: Wayne J. Westplate, 7612 - 33rd Ave., Kenosha, Wis. 53142

[21] Appl. No.: 641,825

[22] Filed: Aug. 17, 1984

[51] Int. Cl.$^4$ .......................... A61F 7/08; A61F 7/10; A63B 21/12; F25D 3/08
[52] U.S. Cl. ................................... 128/402; 62/530; 128/403; 272/119
[58] Field of Search ............... 128/380, 384, 402, 403, 128/DIG. 15; 272/119; 62/530; 126/204

[56] References Cited

U.S. PATENT DOCUMENTS

| | | | |
|---|---|---|---|
| 783,827 | 2/1905 | Gasaway et al. | 128/403 X |
| 1,894,161 | 1/1933 | Crapo | 128/403 |
| 2,562,121 | 7/1951 | Poux | 128/402 X |
| 2,749,914 | 6/1956 | Braley | 128/402 |
| 3,366,380 | 1/1968 | Montour | 272/119 |
| 3,877,426 | 4/1975 | Nirschi | 128/DIG. 15 |
| 3,900,035 | 8/1975 | Welch et al. | 128/402 |
| 4,180,261 | 12/1979 | Kolka | 272/119 |
| 4,247,101 | 1/1981 | Gallmeyer | 272/119 X |
| 4,303,239 | 12/1981 | Walsh | 272/119 |
| 4,324,111 | 4/1982 | Edwards | 62/530 X |

Primary Examiner—Anton O. Oechsle
Attorney, Agent, or Firm—Thomas W. Speckman

[57] ABSTRACT

A therapeutic device featuring a plurality of compartments enclosing a therapeutic substance which may be a refrigerant material which forms a liquid or a slush at temperatures below about 0° C., or a heat releasing substance, or a high density material is provided which may be firmly positioned on various body portions using one or more strap means.

15 Claims, 4 Drawing Figures

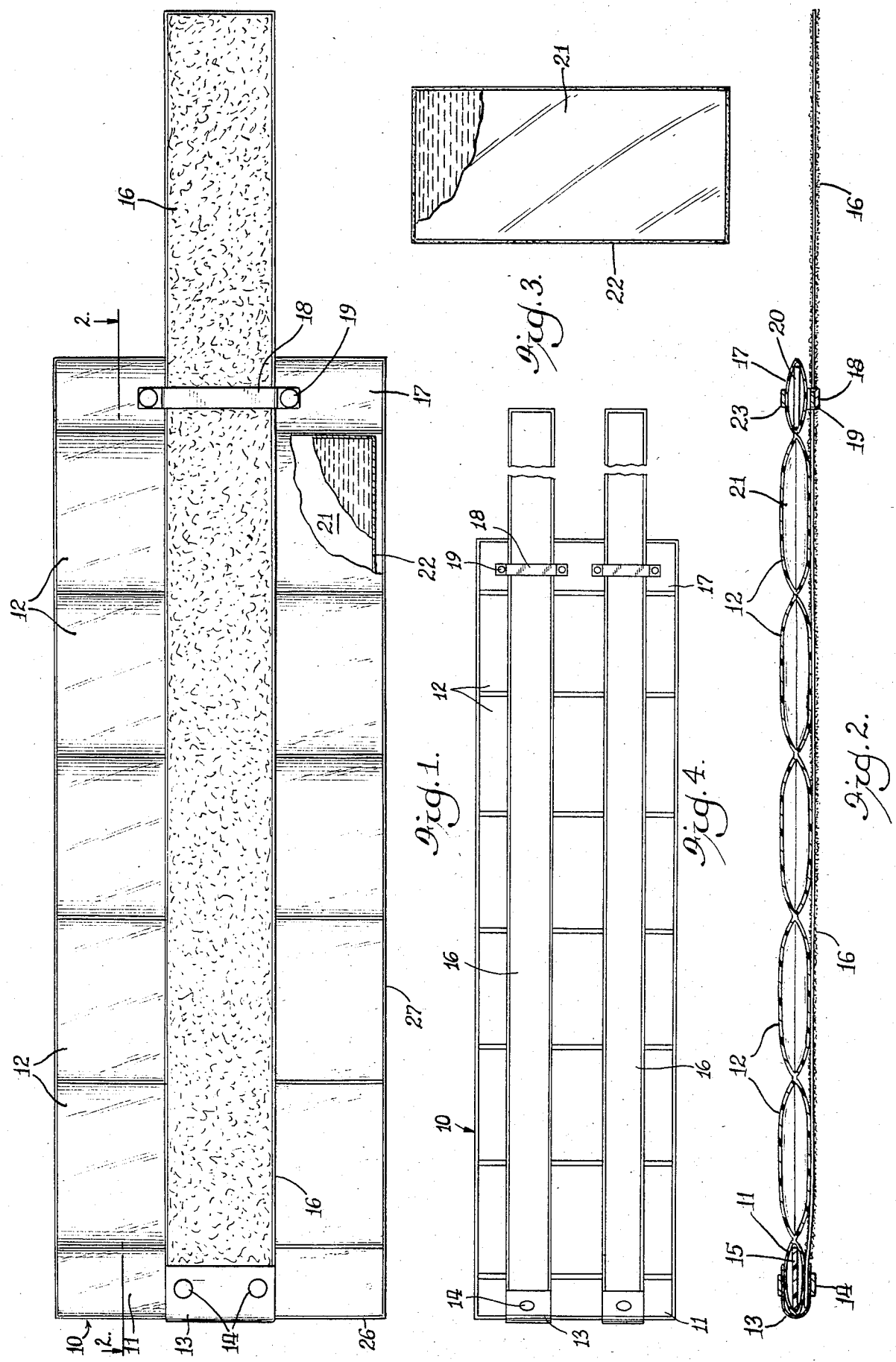

THERAPEUTIC DEVICE

BACKGROUND OF THE INVENTION

1. Field of the Invention

This invention relates to a reusable therapeutic device which may be used for cooling or heating and features a compartmentalized design wherein the device itself is cooled or individual packets are cooled and inserted into a plurality of compartments. Similarly, individual packets may contain a substance which releases heat to bodily injuries. The device may be wrapped around an injured area and fixed by means of one or more straps, so that uniform cooling or heating of the injured area is achieved simultaneously with compression.

2. Description of the Prior Art

Diverse injuries, especially athletic activity related injuries, are preferably treated by immediately applying pressure to and/or cooling the injured area. Compression and cooling both serve to reduce the flow of blood to the injured area so that subsequent swelling, inflammation, and trauma to the area is minimized. Bodily injuries have, for years, been treated by applying ice to the injured area. Ice may satisfactorily cool a bodily injury, but it may be sharp, it must be contained in some containment means to prevent leakage, it cannot be reused, and its application is messy and inconvenient. Other injuries or conditions, such as arthritis, are preferably treated by applying heat to the injured area.

Alternative means to cool injuries have been devised. U.S. Pat. No. 2,366,989 discloses a cooling device comprising a single sealed bag constructed of thin flexible rubber containing a mixture of water with glycerine, glycol or diethylene glycol, or other freezing point depressants, which forms a slush at temperatures below 0° C. This pouch is flexible, may be reused, and is said to conform to body contours.

U.S. Pat. No. 2,378,087 teaches the use of a single flexible container which may be emptied and refilled with various compositions that form a slush at temperatures below 0° C.

U.S. Pat. No. 3,885,403 discloses a single closed flexible envelope which contains a mixture having a gel-like consistency over a wide range of temperatures. This device may be utilized for either heating or cooling applications.

U.S. Pat. No. 2,863,305 is directed primarily to the use of gelling agents in refrigerated compositions. It discloses a packaged dry refrigerant which may be prepared simply by adding water and mixing in a single compartment.

U.S. Pat. No. 3,545,230 teaches a flexible cooling device comprising layered polymer and hydrophilic gels sandwiched between flexible inert substrate material to provide increased cooling capacity.

U.S. Pat. No. 3,736,769 discloses a single cooling container providing walls having different heat transfer rates.

U.S. Pat. No. 4,055,188 teaches a therapeutic wrap in the form of an elongated flexible resilient bandage which carries a refrigerant gel package or hot pack.

U.S. Pat. No. 4,404,820 teaches a cold compress comprising a tough flexible single envelope to enclose a thin gel-like pad which may be supercooled. Insulating material may be directly applied to one surface of the cold compress.

U.S. Pat. No. 3,058,313 teaches a cooling pack constricted to form two pouches for separately storing chemical reactants and when the constriction is released to allow mixture of the chemicals, cooling is provided by a single pouch.

U.S. Pat. No. 3,889,684 discloses a single flexible, fluid impervious envelope filled with a heated or cooled fluid, and having a plurality of flexible strap means.

It is believed that none of the prior art devices achieves the convenience, versatility, economy, or effectiveness provided by the device of the present invention. A single device may be adapted to simultaneously provide compression and to cool a large or a small body surface area, and it will conform to a variety of body contours. The device itself or individual cooling packets may be removed, refrozen, and reused indefinitely, and the device may be firmly fastened to the injured area. The unique combination of features embodied in the present invention is an advance in the treatment and therapy of bodily injuries.

SUMMARY OF THE INVENTION

This invention relates to a therapeutic device which may be used as a reusable cold or hot pack suitable for application to any portion of the body to treat a wide variety of injuries, especially athletic activity related injuries. The therapeutic device comprises a double layer of flexible, non-elastic liquid impervious material which is formed into a plurality of compartments capable of enclosing a therapeutic material which may be a heat releasing substance, or a liquid refrigerant material which forms a liquid or slush at temperatures below about 0° C. Weights may also be inserted into the compartments. One or more flexible non-elastic strap means is attached to the compartmentalized device, to allow firm positioning of the therapeutic device on the injured area, and to provide compression to the injured area, if desired.

The therapeutic device may be produced in a wide variety of shapes and sizes so that it may comfortably and conveniently encircle and conform to any portion of the body. Similarly, any number of strap means may be positioned at various locations on the device, the configuration of strap means designed to accommodate the comfortable and adjustable positioning of the device on any body portion.

The compartments may be sealed on all sides to permanently enclose the desired contents or individual packets of refrigerant or heating material or weights. The compartments may be left open along one side so that cooling or heating packets or weights may be removed and replaced. Cooling and heating packets fit snugly into the compartments so that the surfaces of the cooling or heating packets contact the inner surfaces of the compartment for high thermal transfer. When the therapeutic cooling device contacts the injury, the body heat causes moisture to condense on the outer surface of compartments comprising the cooling device. Moist, uniform cooling is thus provided to the injured area. Flexible, liquid impervious materials which additionally promote the formation of condensation are well known to the art, such as synthetic polymer sheets.

The cooling packet may contain any refrigerant substance which forms a liquid or a slush at temperatures below about 0° C. and has a high cooling capacity, such as propylene glycol and water. Cooling packets may be stored in a freezer, an ice chest, or any sufficiently cold environment until they are needed. The heating packet may contain any suitable heat releasing substance, such as shredded polystyrene foam. The cooling and heating packets slide easily, but snugly, into the compartments, and cold or heat is transferred through the walls of compartments comprising the cooling or heating device, to the injured body area.

The therapeutic device is adaptable for use in many different applications and for many diverse injuries. The device comprises a plurality of compartments, but any number of compartments may actually be filled with cooling or heating packets or weights for any particular application. For example, if the injury is to a small centralized area, one or two cooling or heating packets may be inserted into one or two compartments, the rest remaining empty. Alternatively, to cool or heat a large body area, cooling or heating packets may be inserted into each of several compartments to provide a larger cooling or heating surface area. Additionally, according to one embodiment wherein cooling or heating packets are removable, if a long period of cooling or heating is desired, packets may be removed when their cooling or heating capacity is reduced, and new, cold or hot packets may be easily and conveniently inserted. Thus, a particular body area may be cooled or heated for long periods of time without removing or replacing the therapeutic device itself.

A single therapeutic device according to this invention may be used to cool or heat, simultaneously, two different, but spaced nearby body areas. For example, cooling packets may be inserted into compartments at one end of the therapeutic device and additional cooling packets may be inserted into compartments at the opposite end of the device, to provide cooling to spacially separated body areas. If the cooling device is applied to a leg, the front and the back of the leg may be independently and simultaneously cooled, without cooling the surfaces between.

The cooling or heating device achieves uniform cooling or heating of a small or large surface area. There is a tendency, in prior devices, for the cooling or heating substance to be squeezed into remote parts of a flexible container, especially when the flexible container is folded, or applied to an angular or rounded surface. The compartmentalized design of the present invention precludes such uneven cooling or heating, and the therapeutic cooling or heating device may be applied to angular or rounded surface areas to provide uniform cooling or heating.

Strap means of any suitable material and any suitable dimension may be affixed to the therapeutic device. Non-elastic "Velcro" fasteners straps are convenient and suitable means for most purposes. Back-to-back "Velcro" fasteners straps may be wrapped around an injured area and fastened to themselves so that no additional fastening means are necessary. In one embodiment, a strap means may be affixed to one end of the therapeutic device, and extend for some length beyond the opposite end of the device. Thus, when the therapeutic device is applied to a body surface area, the strap means encircles the outer surface of the device and is sufficiently long to encircle the appropriate body part, and fasten to a portion of itself. The strap means may be retained by a guide affixed to the opposite end of the device. In another embodiment, the strap means is retained by a slot means provided in the opposite end of the device.

Strap means may be affixed to the cooling or heating device at various locations by any suitable attachment means. Suitable attachment means are well known to the art. In one embodiment, the therapeutic device is provided at both ends with a narrow compartment to hold a stabilizing element which may comprise a rigid or a flexible material to provide support for fasteners. A strap attachment means is provided at one end of the device, and firmly affixed to the device by rivets or other fastening means which pass through the firm, stabilizing element. At the opposite end of the therapeutic device, a strap guide may be similarly fixed to the therapeutic device by means of rivets or other fastening means passing through a stabilizing element. The firm stabilizing elements, rigid or flexible, prevent the flexible material comprising the walls of the therapeutic device from ripping or tearing, and provide support for fasteners.

The device may be loosely wrapped around an injured body area when the body area remains stationary, to provide uniform cooling or heating. Alternatively, the therapeutic device may be wrapped more tightly to firmly position the cooling or heating means on the injured area, so that the device is held firmly on the injured area, even during movement. Additionally, the therapeutic device may be tightly wrapped to provide the desired degree of compression to the injured area. Compression to the injured area can be accomplished simultaneously with cooling or heating by means of this therapeutic device.

In addition to heating and cooling packets, packets of variable weights may be similarly accommodated in the compartments of the therapeutic device. The compartments may be permanently sealed to provide a constant amount of weight. Alternatively, if the compartments are open at one end, variable weights may be provided by weighting only selected compartments, or by inserting packets of various weights. The weighted therapeutic device exhibits all of the advantages of the cooling or heating therapeutic device described above, and may be wrapped around or applied to any body surface area. Additionally, if the compartments are open at one end, weight may be applied in combination with heating or cooling operations. This may be especially advantageous if compression to an injured area is desired while simultaneously heating or cooling the area.

BRIEF DESCRIPTION OF THE DRAWINGS

The above mentioned and other features of this invention, and the manner of obtaining them will become more apparent, and the invention will be best understood by reference to the following description of preferred embodiments of the invention, read in conjunction with the accompanying drawings in which:

FIG. 1 is a front view of an apparatus in accordance with one embodiment of this invention;

FIG. 2 is a cross-sectional view of the embodiment illustrated in FIG. 1, taken along line 2—2;

FIG. 3 shows one embodiment of an individual cooling or heating packet suitable for use with this invention; and FIG. 4 is a front view of an apparatus having a plurality of strap means in accordance with one embodiment of this invention

DESCRIPTION OF THE PREFERRED EMBODIMENTS

As shown in FIG. 1, therapeutic device 10 comprises a plurality of individual packet compartments 12. The number of individual compartments comprising the therapeutic wrap depends upon the length of the wrap, the degree of flexibility desired, and the duration of desired heating or cooling. Three or more compartments are preferred. The number of compartments may be increased to provide for greater flexibility of the device. Larger compartments will provide longer lasting heating or cooling effects. Several embodiments may thus provide various numbers of compartments to best achieve the heating or cooling effect desired.

Therapeutic cooling, heating, or weighted device 10 comprises a double layer of durable, flexible, liquid impervious material. A liquid impervious plastic material which retains flexibility at temperatures below about 0° C. and promotes the formation of condensation is preferred, such as synthetic polymeric sheets. Suitable materials are known to the art.

As shown in FIG. 1, therapeutic device 10 comprises a plurality of compartments. The double lines represent portions of the device where the inner and outer layers of the double layers are permanently sealed. The double layers may be hermetically sealed, at least along edges 26, 27 and 28, and between each of the individual compartments 12. The therapeutic device may be sealed along top edge 29 or it may be left open to permit removal of individual packets from compartments 12.

Heating, cooling, or weighted packets 21, hermetically sealed along all edges 22, fit snugly into compartments 12 so that the walls of packets 21 contact the walls of compartments 12. An individual cooling packet may contain any refrigerant material which forms a liquid or a slush at temperatures below about 0° C., such as mixtures of propylene glycol and water. Individual heating packets may contain any suitable heat releasing substance. Individual weighted packets may contain any material of relatively high density and which provides sufficient flexibility. Suitable cooling, heating and weighted compounds are known to the art.

Strap means to firmly position the therapeutic device on the desired body portion may be affixed to therapeutic device 10 at various locations. The number and configuration of strap means may vary, as shown in FIG. 4. A plurality of strap means may be desired to comfortably and firmly position a large therapeutic device over a large body surface area and a single strap means may be desired to position a smaller therapeutic device. Strap means may be affixed to the therapeutic device by any suitable attachment means.

As shown in FIG. 1, single strap means 16 is affixed to one end portion 11 of therapeutic device 10 and extends for a distance beyond opposite end portion 17 of therapeutic device 10. When therapeutic device 10 is wrapped around or applied to a bodily injury, strap means 16 is sufficiently long to encircle therapeutic device 10 and provide an extending fastening portion. As shown in FIGS. 1 and 2, strap means 16 is preferably constructed of back-to-back "Velcro" fasteners. This construction permits the device to be wrapped around the body portion and the extending strap means may then be firmly attached to itself. The distal portion of strap means 16 may extend around the body portion and the underside of the distal portion of strap means 16 may be firmly attached to the upperside of strap means 16 near, but for a portion beyond, strap attachment means 13. Other suitable strap and fastening means, such as straps with buckles or other suitable attachment means, may be provided to firmly position therapeutic device 10 on any bodily injury.

In one embodiment, shown in FIGS. 1 and 2, strap means 16 is permanently affixed to one end of therapeutic device 10 by strap attachment means 13. Strap attachment means 13 is substantially symmetrically U-shaped and may be rigid. Strap attachment means 13 may be slidably fitted over edge 26, to grip device end portion 11 and the end portion of strap means 16. Strap attachment means 13 may be permanently affixed to therapeutic device 10 utilizing any suitable fastening means.

In the embodiment shown in FIGS. 1 and 2, end portion 11 is specially provided for the attachment of strap means 16. End portion 11 forms a separate compartment in which strap attachment stabilizer 15, which may be rigid or flexible, is inserted. Rivets 14, or similar fastening means, extend through strap attachment means 13, strap means 16, strap attachment stabilizer 15, and both layers of therapeutic device 10, and are affixed to the corresponding opposite portion of strap attachment means 13. This method of strap attachment assures that the strap is firmly and permanently attached, and that the walls of the device will not rip or tear when pressure is exerted on the strap means.

In one embodiment, strap guide means 18 may be similarly attached to therapeutic device 10 on an opposite end portion 17. Rivets 19, or other suitable fastening means, extend through strap guide means 18, through guide means stabilizer 20, through both layers of end portion 17, and are permanently affixed to flat guide attachment means 23. Strap guide means 18 has flat portions on either end for attachment of rivets 19, and is raised by slightly more than the height of strap means 16, for slightly more than the width of strap means 16. In this way, strap means 16 is positioned by strap guide means 18. Flat attachment means 23 has approximately the same dimensions as strap guide means 18, but is flat along its entire length. In another embodiment, the strap means may be retained by a slot means provided in the opposite end of the device. Alternatively, the strap means does not require any retaining means to secure or guide the strap means.

The apparatus of this invention may be constructed of materials and components apparent to one skilled in the art upon reading this disclosure. Likewise, the specific design and sizing parameters will be apparent to one skilled in the art upon reading this disclosure.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

I claim:

1. A therapeutic device comprising:
   an elongated double layer of flexible, non-elastic liquid impervious material divided into a plurality of compartments and provided at both ends with a narrow compartment enclosing a stabilizing element;
   at least one said compartment containing therapeutic material;
   at least one flexible, non-elastic strap means permanently fixed to one end of said device, a strap attachment means provided at said one end of said device and affixed to said device by fastening means passing through one of said stabilizing elements and a strap guide means provided at the opposite end of said device and affixed to said device by fastening means passing through the other of said stabilizing elements, whereby said device may be firmly positioned on a body portion.

2. the therapeutic device of claim 1 wherein at least one sealed packet containing therapeutic material is fit snugly into at least one said compartment, the outer surfaces of said sealed packet contacting the inner surfaces of said compartment.

3. The therapeutic device of claim 2 wherein said therapeutic material comprises a refrigerant substance having a high cooling capacity which forms a liquid or a slush at temperatures below about 0° C.

4. The therapeutic device of claim 2 wherein said therapeutic material comprises a heat releasing substance.

5. The therapeutic device of claim 2 wherein said therapeutic material comprises a high density weighted compound.

6. the therapeutic device of claim 2 wherein said compartments are permanently sealed on all sides.

7. The therapeutic device of claim 2 wherein said compartments are permanently sealed on three sides and open along a fourth side.

8. The therapeutic device of claim 1 wherein said therapeutic material comprises a refrigerant substance having a high cooling capacity which forms a liquid or a slush at temperatures below about 0° C.

9. The therapeutic device of claim 1 wherein said therapeutic material comprises a heat releasing substance.

10. The therapeutic device of claim 1 wherein said therapeutic material comprises a high density weighted compound.

11. The therapeutic device of claim 1 wherein said compartments are permanently sealed on all sides.

12. The therapeutic device of claim 1 wherein said compartments are permanently sealed on three sides and open along a fourth side.

13. The therapeutic device of claim 1 wherein said device is provided with between 3 and 9 compartments.

14. The therapeutic device of claim 1 wherein said strap means comprises "Velcro" fasteners.

15. The therapeutic device of claim 1 wherien said device is provided with a plurality of strap means.

* * * * *